US010875019B2

(12) United States Patent
Xu et al.

(10) Patent No.: US 10,875,019 B2
(45) Date of Patent: Dec. 29, 2020

(54) MULTI-FLUX MICROFLUIDIC CHIP FOR NUCLEIC ACID DETECTION AND CAPABLE OF ACTIVELY CONTROLLING FLOW PATH, AND USE METHOD THEREOF

(71) Applicant: Lansion Biotechnology Co., Ltd., Jiangsu (CN)

(72) Inventors: Xingshang Xu, Jiangsu (CN); Jeffery Chen, Jiangsu (CN); Tao Zhu, Jiangsu (CN); Pei Yu, Jiangsu (CN)

(73) Assignee: Lansion Biotechnology Co., Ltd., Jiangsu (CN)

( * ) Notice: Subject to any disclaimer, the term of this patent is extended or adjusted under 35 U.S.C. 154(b) by 51 days.

(21) Appl. No.: 16/077,482

(22) PCT Filed: Dec. 6, 2017

(86) PCT No.: PCT/CN2017/114693
§ 371 (c)(1),
(2) Date: Aug. 12, 2018

(87) PCT Pub. No.: WO2019/061816
PCT Pub. Date: Apr. 4, 2019

(65) Prior Publication Data
US 2019/0351412 A1    Nov. 21, 2019

(30) Foreign Application Priority Data

Sep. 26, 2017  (CN) .......................... 2017 1 0878470

(51) Int. Cl.
*C12Q 1/68* (2018.01)
*B01L 3/00* (2006.01)
(Continued)

(52) U.S. Cl.
CPC ... *B01L 3/502715* (2013.01); *B01L 3/502707* (2013.01); *B01L 7/52* (2013.01);
(Continued)

(58) Field of Classification Search
CPC ......... B01L 3/502707; B01L 3/502715; B01L 7/52; B01L 2300/0864; B01L 2300/0887;
(Continued)

(56) References Cited

U.S. PATENT DOCUMENTS

| 2002/0001848 A1* | 1/2002 | Bedingham ....... B01L 3/502707 436/45 |
| 2008/0003145 A1* | 1/2008 | Nurse ............... B01L 3/502738 422/400 |

(Continued)

FOREIGN PATENT DOCUMENTS

| CN | 1968754 | 5/2007 |
| CN | 101003010 | 7/2007 |

(Continued)

*Primary Examiner* — Betty J Forman
(74) *Attorney, Agent, or Firm* — JCIPRNET (57) ABSTRACT

The present invention discloses a multi-flux microfluidic chip for nucleic acid detection and capable of actively controlling a flow path, and a use method thereof. The detection chip includes a chip body, and the chip body is provided with a sample loading chamber, a reaction chamber, and a microfluidic channel, where there is a plurality of reaction chambers, and the microfluidic channel includes a sample output main channel and several sample distribution channels. The sample distribution channels are separately disposed, and include sample distribution chamber sample output channels and reaction chamber sample input channels, where the sample distribution chamber sample output channels and the reaction chamber sample input channels can be communicated through sample distribution connection channels formed through heat sealing processing for a thin film on the chip body, and a thin film part of the sample distribution connection channel can form a sample distribution occlusion portion after undergoing heat sealing processing, to intercept the flow in the sample distribution channels. Therefore, the present invention uses heat sealing technol- (Continued)

ogy to replace a micro valve to control opening/closing of a channel, so as to decrease the number of parts mounted on the microfluidic chip, and reduce the continuous work of an instrument and energy consumption thereof. Moreover, the present invention achieves a multi-flux detection effect.

8 Claims, 5 Drawing Sheets

(51) Int. Cl.
    *B01L 7/00*     (2006.01)
    *C12Q 1/686*     (2018.01)

(52) U.S. Cl.
    CPC ...... *C12Q 1/686* (2013.01); *B01L 2300/0681* (2013.01); *B01L 2300/0816* (2013.01); *B01L 2300/0819* (2013.01); *B01L 2300/0825* (2013.01); *B01L 2300/0864* (2013.01)

(58) Field of Classification Search
    CPC ............. B01L 2300/0861; C12Q 1/686; F16K 99/0042
    See application file for complete search history.

(56) References Cited

U.S. PATENT DOCUMENTS

2008/0193336 A1\*   8/2008   Cho ................... B01L 3/50273
                                                        422/400
2015/0298129 A1\*   10/2015   Dugan ............... B01L 3/50851
                                                       435/286.1

FOREIGN PATENT DOCUMENTS

CN           101674888         3/2010
KR         20100128518      12/2010

\* cited by examiner

MULTI-FLUX MICROFLUIDIC CHIP FOR NUCLEIC ACID DETECTION AND CAPABLE OF ACTIVELY CONTROLLING FLOW PATH, AND USE METHOD THEREOF

CROSS-REFERENCE TO RELATED APPLICATION

This application is a 371 application of the international PCT application serial no. PCT/CN2017/114693, filed on Dec. 6, 2017, which claims the priority benefit of China application no. 201710878470.1, filed on Sep. 26, 2017. The entirety of each of the abovementioned patent applications is hereby incorporated by reference herein and made a part of this specification.

BACKGROUND

Technical Field

The present invention relates to the field of microfluidics, and in particular, to a multi-channel microfluidic chip of a heat-sealed structure.

The present invention further relates to a method of using the above microfluidic chip for nucleic acid detection.

Description of Related Art

Most of current microfluidic chips have one reaction hole. One chip can implement detection for only one pathogen, thus failing to achieve detection requirements of the microfluidic chips in terms of flux.

In addition, in microfluidics, an accurate flow of fluid is controlled using a valve. Valves in the current microfluidic chips are mostly actuated by a pressure or mechanical force, which can only occlude a flow path. After the pressure or mechanical force disappears, the flow path reverts to an unimpeded state. For a reaction that requires a sealed condition in a whole course, an instrument is required to unceasingly apply a pressure or mechanical force, and multiple valves further need to be used. As a result, the structure of the microfluidic chip may become rather complex, there is complicated requirements on the instrument, and the price is high, failing to facilitating large-scale assembly and use.

To sum up, how to provide a microfluidic chip that has multiple channels, and can equally distribute a reagent among reaction chambers, enable the temperature of the reagent to rapidly increase/decrease, and control impermeability of a reaction fluid is a problem in urgent need to be solved, so as to decrease the number of parts mounted on the microfluidic chip, and reduce the continuous work of the instrument and energy consumption thereof, thus facilitating assembly and operation.

SUMMARY OF THE INVENTION

For the deficiencies in the prior art, the present invention provides a multi-flux microfluidic chip for nucleic acid detection and capable of actively controlling a flow path. The microfluidic chip has multiple channels, and can equally distribute a reagent among reaction chambers, enable the temperature of the reagent to rapidly increase/decrease, and control impermeability of a reaction fluid, so as to decrease the number of parts mounted on the microfluidic chip, and reduce the continuous work of an instrument and energy consumption thereof, thus facilitating assembly and operation.

To achieve the foregoing technical objective, the present invention adopts the following technical solutions:

A multi-flux microfluidic chip for nucleic acid detection and capable of actively controlling a flow path includes: a chip body, provided with a sample loading chamber, a reaction chamber, and a microfluidic channel, where the sample loading chamber is communicated with an external air path and a sample output through hole of the sample loading chamber is communicated with the reaction chamber through the microfluidic channel; there is a plurality of reaction chambers, and the microfluidic channel includes a sample output main channel and several sample distribution channels disposed in one-to-one correspondence to the reaction chambers; and the sample distribution channels are separately disposed, and include sample distribution chamber sample output channels and reaction chamber sample input channels, where:

one end of the sample output main channel is communicated with the sample output through hole of the sample loading chamber, and the other end is communicated with the sample distribution chamber;

the reaction chambers are arranged in two rows that are symmetrically distributed on two sides of the sample distribution chamber with the axis of the sample output main channel as a line of symmetry;

the sample distribution chamber sample output channels of the sample distribution channels are evenly distributed on the periphery of the sample distribution chamber, and the reaction chamber sample input channels are symmetrically distributed on two sides of the sample distribution chamber with the axis of the sample output main channel as a line of symmetry; and each sample distribution chamber sample output channel and its corresponding reaction chamber sample input channel are communicated through a sample distribution connection channel formed through heat sealing processing for a thin film on the chip body; each sample distribution connection channel extends across the corresponding sample distribution chamber sample output channel and reaction chamber sample input channel; and a thin film part of the sample distribution connection channel can form a sample distribution occlusion portion after undergoing heat sealing processing, to intercept the flow in the sample distribution channels.

As a further improvement to the present invention, the chip body is further provided with a filter element passage and a test paper passage in communication with a liquid outlet of the filter element passage; wherein: a breathable and liquid-impermeable filter element is provided in the filter element passage, and color indicator paper is provided in the test paper passage; the reaction chamber is provided with an outlet, and the outlet of the reaction chamber can be communicated with an inlet of the filter element passage through an overflow passage formed through heat sealing processing for a thin film on the chip body, the overflow passage extending across the outlet of the reaction chamber and the inlet of the filter element passage; and a thin film part of the overflow passage can form an overflow occlusion portion after undergoing heat sealing processing, to intercept the flow at the outlet of the reaction chamber.

As a further improvement to the present invention, there is a plurality of filter element passages arranged in one-to-one correspondence to the reaction chambers, and the liquid outlets of the filter element passages converge in communication with the test paper passage; and there are two test paper passages that are correspondingly arranged outside of the two rows of the reaction chambers.

As a further improvement to the present invention, the chip body includes an upper thin film, an upper-layer chip, a lower-layer chip, and a lower thin film, where the upper-layer chip is partitioned into a sample loading zone and a reaction zone; a sample loading pool is provided on the sample loading zone of the upper-layer chip, a sample loading chamber is formed by putting a plug in a sample loading hole of the sample loading pool, and the sample output through hole of the sample loading chamber is disposed on the bottom of the sample loading pool; the reaction zone of the upper-layer chip is provided with a sample inlet hole of the sample distribution connection channel and a sample outlet hole of the sample distribution connection channel separately; and the sample output through hole of the sample loading chamber, the sample inlet hole of the sample distribution connection channel, and the sample outlet hole of the sample distribution connection channel are all through holes vertically running through the upper-layer chip;

the lower-layer chip is located below the upper-layer chip, and is connected to a lower surface of the upper-layer chip in a bonding manner; and the lower-layer chip is provided with a lower-layer chip reaction zone on a position corresponding to the reaction zone of the upper-layer chip;

the lower-layer chip reaction zone is provided with a sample distribution pool, a reaction pool, a sample distribution chamber sample output channel, and a reaction chamber sample input channel; a sample distribution chamber is formed after the sample distribution pool is covered by the lower surface of the upper-layer chip, and the sample distribution pool is communicated with the sample output through hole disposed on the bottom of the sample loading pool through the sample output main channel disposed on the lower-layer chip; and a reaction chamber is formed by sealing the reaction pool with a reaction pool upper cover disposed on a corresponding position on the lower surface of the upper-layer chip and through heat sealing for the lower thin film;

the sample inlet hole of the sample distribution connection channel is disposed directly above the sample outlet of the sample distribution chamber sample output channel, and the sample outlet hole of the sample distribution connection channel is disposed directly above the sample inlet of the reaction chamber sample input channel; and the upper thin film covers an upper surface of the reaction zone of the upper-layer chip, and a sample distribution connection passage can be formed between the sample inlet hole of the sample distribution connection channel and the sample outlet hole of the sample distribution connection channel after the upper thin film undergoes heat sealing processing by a heat sealing device; in addition, a thin film part of the sample distribution connection passage can also form a sample distribution occlusion portion after a heat sealing device performs heat sealing processing thereon, to intercept the flow in the sample distribution passage.

As a further improvement to the present invention, the lower thin film covers a lower surface of a reaction zone of the lower-layer chip, and the bottom of each reaction pool is formed by the lower thin film.

As a further improvement to the present invention, for each reaction pool, the reaction zone of the upper-layer chip is provided with an overflow passage sample inlet hole and an overflow passage sample outlet hole; and the overflow passage sample inlet hole and the overflow passage sample outlet hole are both through holes vertically running through the upper-layer chip, and the overflow passage sample inlet hole is arranged to just run through the reaction pool upper cover;

after the heat sealing device performs heat sealing processing on the upper thin film, an overflow passage can be formed between the corresponding overflow passage sample inlet hole and overflow passage sample outlet hole; and in addition, a thin film part of the overflow passage can also form an overflow occlusion portion after the heat sealing device performs heat sealing processing thereon, to intercept the flow at the outlet of the reaction chamber;

the overflow passages are arranged in two rows that are correspondingly distributed outside of the corresponding reaction pool;

an upper surface of the lower-layer chip is provided with a through hole in communication with the filter element passage on a position corresponding to each overflow passage sample outlet hole;

the number of the filter element passages is the same as that of the overflow passage sample outlet holes, and the filter element passages are arranged below the overflow passage sample outlet holes in rows; the filter element passages are arranged on the lower surface of the lower-layer chip, a breathable and liquid-impermeable filter element is provided in each filter element passage, and liquid outlets of the filter element passages in each row converge in communication with a test paper passage; and the test paper passage is provided on the back side of the lower-layer chip, and positioned outside of the filter element passage.

As a further improvement to the present invention, the heat sealing device includes a heat sealing cover provided with a channel block and a heat sealing block, where:

the channel block is provided with mold recesses a and mold recesses b; the mold recess a matches up with the sample distribution connection passage in size, and a distribution condition of the mold recesses a on the channel block is consistent with that of the sample distribution connection passages on the upper-layer chip; the mold recess b matches up with the overflow passage in size, and a distribution condition of the mold recesses b on the channel block is consistent with that of the overflow passages on the upper-layer chip; and the heat sealing block is provided with a mold protrusion a and a mold protrusion b; the mold protrusion a includes two protruding bars, and the two protruding bars can respectively press against thin film parts of the overflow passages in two rows; the mold protrusion b is an annular protrusion that can press against thin film parts of the sample distribution connection passages.

As a further improvement to the present invention, the upper-layer chip and the lower-layer chip are integrally bonded by connecting a cylinder and a positioning hole in a fitted manner.

As a further improvement to the present invention, a reaction dry powder reagent required for a polymerase chain reaction (PCR) is pre-embedded in the reaction chamber, the reagent including an enzyme, primer, probe and buffer solution required for the PCR reaction.

Another technical objective of the present invention is to provide a method of using a multi-flux microfluidic chip for nucleic acid detection and capable of actively controlling a flow path, which includes the following steps:

1) assembling an upper-layer chip and a lower-layer chip into an integral body through a bonding manner;

2) using a channel block of a heat sealing device to perform heat sealing processing on an upper thin film, such that overflow passages and sample distribution connection passages are formed between the upper thin film and the upper-layer chip, where in this case, a microfluidic channel between a sample loading pool and a reaction pool is in an opened state, and a microfluidic channel between the reaction pool and a filter element passage is also in an opened state;

3) pre-embedding a reaction dry powder reagent required for a PCR reaction in the reaction pool of the lower-layer chip, pre-disposing a breathable and liquid-impermeable filter element in the filter element passage, and pre-disposing color indicator paper in a test paper passage;

4) covering a reaction zone of a lower surface of the lower-layer chip with a lower thin film, and performing heat sealing processing;

5) adding a sample into the sample loading pool;

6) mounting an external air path at a sample inlet of the sample loading pool; connecting to an air source, and under an air pressure provided by the air source, the sample in the sample loading pool passing through a sample output main channel and a sample distribution chamber successively, and flowing to a corresponding reaction pool through sample distribution chamber sample output channels, the sample distribution connection passages, and reaction chamber sample input channels; after the sample flowing out of the reaction pools enters the filter element passages through the overflow passages, an instrument stopping flow of the external air path by detecting a pressure value;

7) using a heat sealing block of the heat sealing device to perform heat sealing processing on the upper thin film, such that an overflow occlusion portion is formed between a thin film part of each overflow passage and the upper-layer chip, and a sample distribution occlusion portion is formed between a thin film part of each sample distribution connection passage and the upper-layer chip, where in this case, the front end and the rear end of the reaction pool are both in a flow intercepted state and the reaction pools are closed;

8) closing a chip plug;

9) the sample and the reaction dry powder reagent in the reaction pool producing a PCR reaction; and 10) reading fluorescent data after completion of the reaction.

According to the foregoing technical solutions, the present invention has the following advantages as compared with the prior art:

1. In the present invention, by using a microfluidic channel of a specific structure and form, a sample can be distributed from one sample chamber to multiple reaction chambers at the same time, thus achieving a multi-flux effect. The detection efficiency is improved and resource consumption is greatly reduced.

2. In the present invention, opening/closing of the microfluidic channels on the front end and the rear end of the reaction chambers (reaction pools) is not controlled by a valve, but by some flow paths (sample distribution connection passages and overflow passages) formed in the microfluidic channels through heat sealing for a thin film, such that the whole microfluidic channel is in an opened state. Alternatively, through the heat sealing process for a thin film, a channel occlusion portion is formed in the flow paths having a thin film, to intercept the flow in the microfluidic channel. Thus, the flow in the front end and the rear end of the reaction chambers is intercepted, and the reaction chambers are closed. It can be known from the above that, the present invention uses heat sealing technology to directly replace all closure valves on the chip, thus facilitating processing and operation, saving resources, and realizing really closed chambers, so that the experiment place is prevented from aerosol pollution.

3. The sample distribution connection passages and overflow passages in the present invention are all located above the front-end and rear-end microfluidic channel connected thereto, thus preventing backflow.

BRIEF DESCRIPTION OF THE DRAWINGS

In the figure: Plug 1; Upper thin film 2; Upper-layer chip 3; Lower-layer chip 4; Filter element 5; Test paper 6; Lower thin film 7.

In the figure: Chip body 8.

In the figure: Heat-sealing cover 10; Mold recess b 11-1; Mold recess a 11-1; Channel block 12; Heat sealing block 13; Mold protrusion a14-1; Mold protrusion b14-2.

In the figure: Upper-layer chip 3; Sample outlet hole of a sample distribution connection channel 15; Sample outlet hole of an overflow passage 16; Sample loading pool 17; Sample output through hole of the sample loading pool 18; Air path connector 19.

In the figure: Lower surface of the upper-layer chip 20; Upper end of a connection through hole of a filter element passage 21; Reaction pool upper cover 22; Cylinder 23.

In the figure: Lower-layer chip 4; Positioning hole 24; Reaction pool 25; Sample distribution pool 26; Sample output main channel 27; Reaction pool sample input channel 28; Sample distribution chamber sample output channel 29; Lower end of a connection through hole of a filter element passage 30.

In the figure: Reaction pool bottom 31; Lower surface of lower-layer chip 32; Test paper passage 33; Filter element passage 34.

In the figure: Upper thin film 2; sample distribution connection channel 36; Overflow passage 35.

DETAILED DESCRIPTION OF THE EMBODIMENTS

The technical solutions of the embodiments of the present utility model are clearly and completely described below with reference to the accompanying drawings of the embodiments of the present utility model. Apparently, the described embodiments are some rather than all of the embodiments of the present utility model. The following description of at least one exemplary embodiment is merely illustrative in nature and is in no way intended to pose any limitation on the present utility model and its application or use. Based on the embodiments of the present utility model, other embodiments acquired by those of ordinary skill in the art without creative effort all belong to the protection scope of the present utility model. Unless specifically stated otherwise, the relative arrangements, expressions, and values of the components and steps set forth in these embodiments do not limit the scope of the present utility model. In addition, it should be understood that for ease of description, the dimensions of the various parts shown in the drawings are not drawn in accordance with actual scale relationships. Techniques, methods, and apparatuses known to those of ordinary skill in the relevant art may not be discussed in detail, but the techniques, methods and apparatuses should be considered as part of the authorized specification if appropriate. In all examples shown and discussed herein, any specific value should be interpreted to be illustrative only but not restrictive. Therefore, other examples of the exemplary embodiments may have different values.

For ease of description, spatially relative terms such as "on", "above", "on the surface of", "upper", etc. may be used herein to describe a spatial positional relationship between one device or feature and another device or feature as shown in the figures. It should be understood that the spatially relative terms are intended to encompass different orientations of the device in use or operation in addition to the orientation of the device depicted in the figures. For example, if a device in the figures is turned upside down, the device described as "above other devices or structures" or "on other devices or structures" will be positioned as "below other devices or structures" or "under other devices or structures". Thus, the exemplary term "above" may include both orientations of "above" and "below", and the device may also be positioned in other different manners (the device is rotated by 90 degrees or positioned in other orientations).

As shown in FIG. 1 to FIG. 9, the present invention provides a multi-flux microfluidic chip for nucleic acid detection and capable of actively controlling a flow path, which includes a chip body, provided with a sample loading chamber, a reaction chamber, a sample distribution chamber, and a microfluidic channel, where the sample loading chamber is communicated with an external air path, and a sample output through hole of the sample loading chamber is communicated with the reaction chamber through the microfluidic channel. The chip body includes an upper thin film, an upper-layer chip, a lower-layer chip, and a lower thin film that are arranged successively from top to bottom.

The upper-layer chip and the lower-layer chip are integrated after insertion through alignment holes, and are bonded by a technique such as heat bonding, ultrasound or laser. The upper-layer chip is partitioned into a sample loading zone and a reaction zone. The lower-layer chip is provided with a lower-layer chip reaction zone on a position corresponding to the reaction zone of the upper-layer chip. The upper thin film covers an upper surface of the reaction zone of the upper-layer chip, and the lower thin film covers a lower surface of the lower-layer chip reaction zone. The lower thin film is made from a thin-layer polymer material such as polypropylene (PP), polyethylene (PE), or polystyrene (PS).

Figure 1:
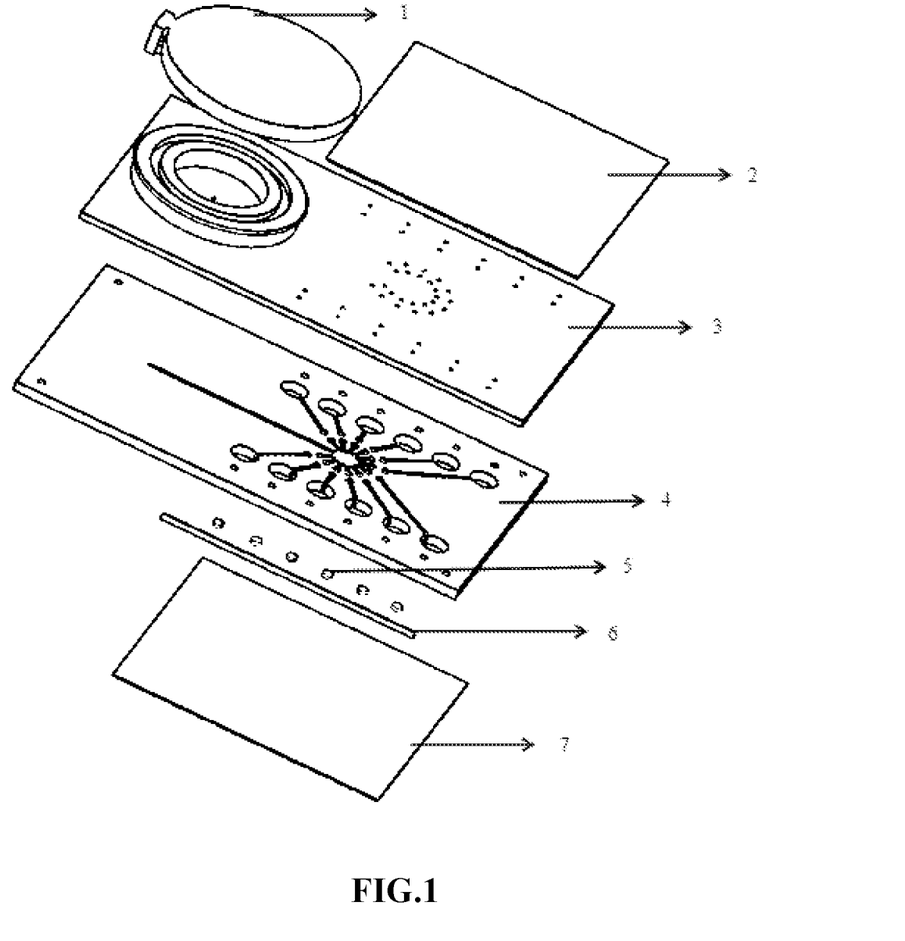
FIG. 1 is a schematic structural diagram of a microfluidic chip for nucleic acid detection according to the present invention.
Figure 5:
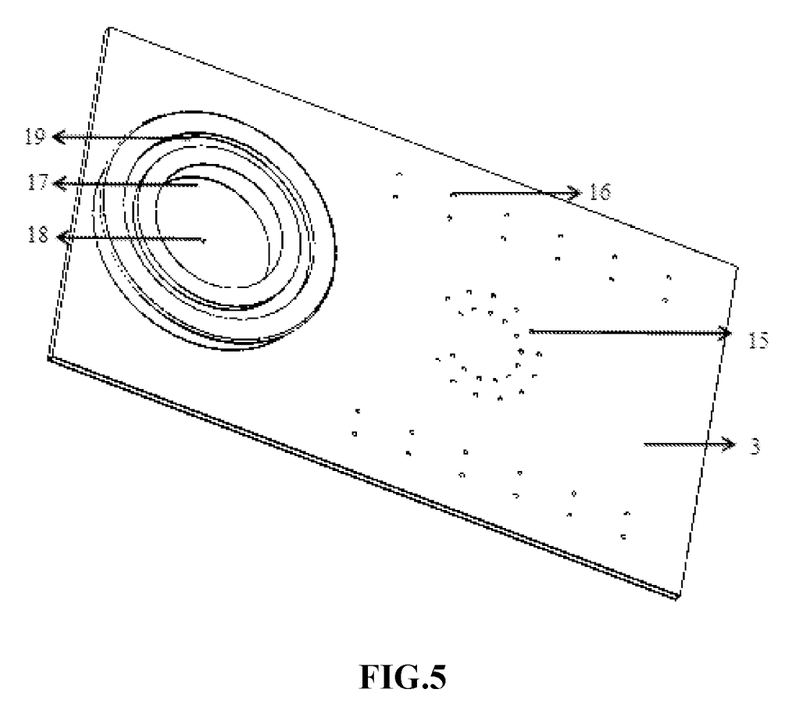
FIG. 5 is a schematic structural diagram of a front side of an upper-layer chip.
Figure 6:
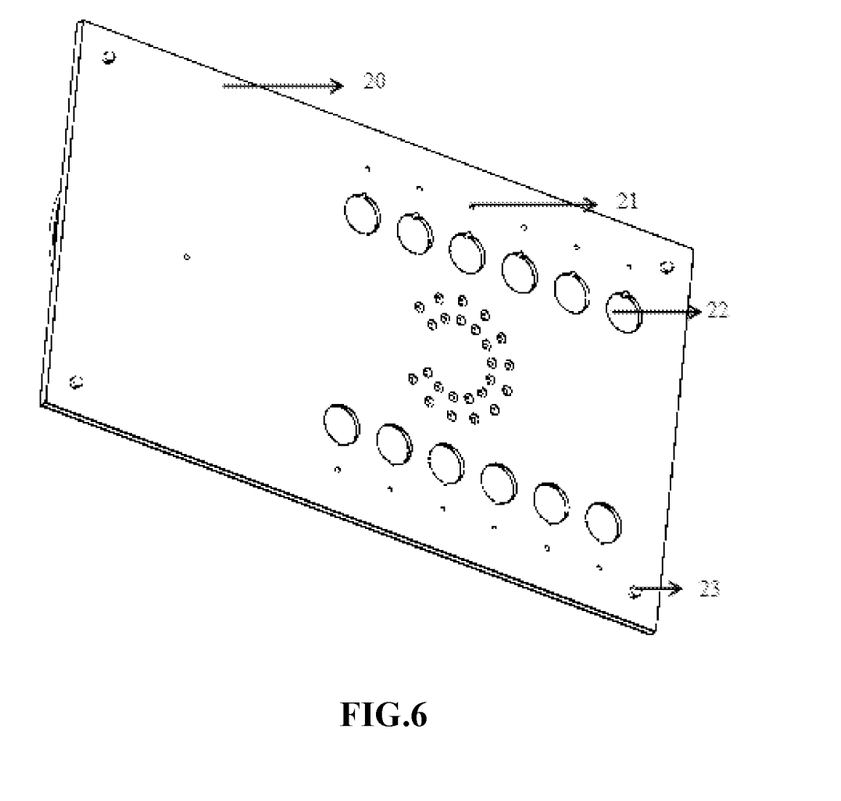
FIG. 6 is a schematic structural diagram of a back side of the upper-layer chip.

The sample loading chamber is used to store a sample; and includes, as shown in FIGS. 1, 5 and 6, a sample loading pool. An opening of the sample loading chamber is provided with a plug, and an air path connector 19 is disposed at the opening of the sample loading pool. After completion of sample loading, the sample loading chamber is connected to an air path through the air path connector 19, to deliver, under thrust of an air pump, the sample to the microfluidic channel through the sample output through hole 18 disposed on the bottom of the sample loading pool. The sample loading pool is disposed on a sample loading zone of the upper-layer chip.

Figure 7:
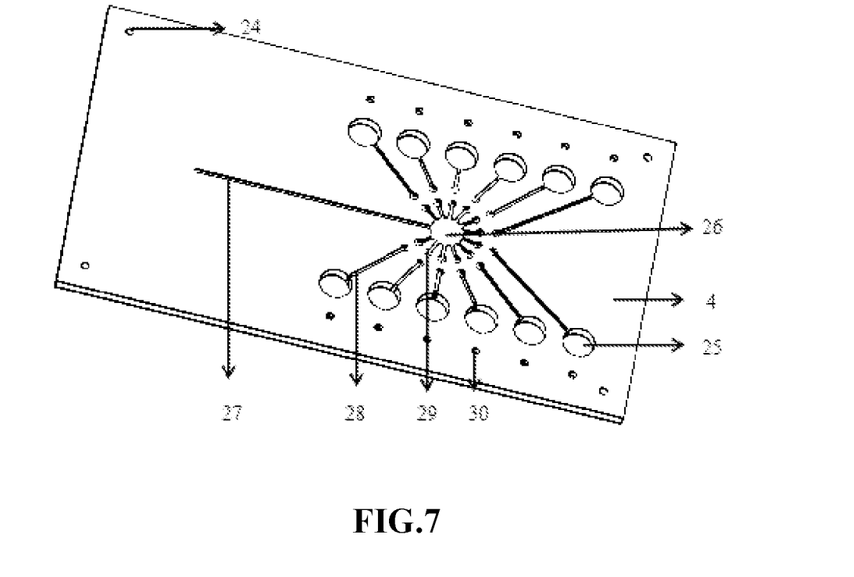
FIG. 7 is a schematic structural diagram of a front side of a lower-layer chip.
Figure 8:
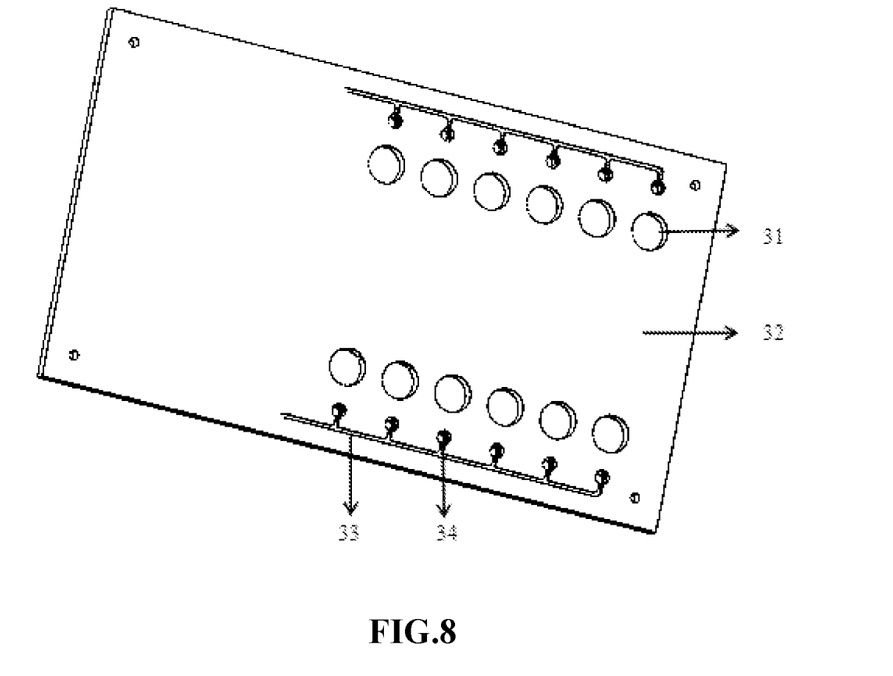
FIG. 8 is a schematic structural diagram of a back side of the lower-layer chip.

A reaction dry powder reagent required for a reaction is pre-embedded in the reaction chamber, where the dry powder reagent includes an enzyme, primer, probe and buffer solution required for a PCR reaction. As shown in FIGS. 1, 7 and 8, the reaction chamber includes a reaction pool upper cover, a reaction pool, and a reaction pool bottom. The reaction pool upper cover is disposed on the lower surface of the upper-layer chip, the reaction pool is disposed on the lower-layer chip, and the reaction pool bottom is formed by the lower thin film. The three are connected in a sealed manner from top to bottom to form the reaction chamber. During reaction in the reaction chamber, a reaction liquid expands with heat, and the reaction pool bottom formed by the lower thin film deforms to a certain degree for mitigation. After completion of the reaction, data is read through fluorescence detection. In addition, there is a plurality of reaction chambers in the present invention. There are 12 reaction chambers shown in the figures, which are arranged in two rows each having six ones.

As shown in FIGS. 1, 7 and 8, the microfluidic channel includes a sample output main channel and several sample distribution channels disposed in one-to-one correspondence to the reaction chambers. In the figures, there are 12 sample distribution channels in one-to-one correspondence to the 12 reaction chambers. The sample distribution channels are separately disposed, and include sample distribution chamber sample output channels and reaction chamber sample input channels. One end of the sample output main channel is communicated with the sample output through hole of the sample loading chamber, and the other end is communicated with the sample distribution chamber.

The sample distribution chamber includes a sample distribution pool. The sample distribution pool is disposed on an upper surface of a reaction zone of a middle-layer chip, and an opening of the sample distribution pool is sealed with the lower surface of the reaction zone of the upper-layer chip.

The sample output main channel is arranged on the upper surface of the middle-layer chip along one of center lines on the middle-layer chip. One end of the sample output main channel is communicated with the sample output through hole on the bottom of the sample loading pool, and the other end is communicated with the sample distribution pool.

In the figures, there are 12 sample distribution chamber sample output channels disposed on the upper surface of the middle-layer chip. The sample distribution chamber sample output channels are each communicated with the sample distribution pool, and annularly disposed around the sample distribution pool, and symmetrically arranged about the axis of the sample output main channel.

There are 12 reaction chamber sample input channels, and are arranged in two rows on the upper surface of the middle-layer chip. The reaction chamber sample input channels are each communicated with the reaction pool. The reaction chamber sample input channels arranged in rows are symmetrically disposed about the axis of the sample output main channel.

Through holes are opened on the upper-layer chip, and vertically run through it at positions corresponding to outlets of the sample distribution chamber sample output channels, to form sample inlet holes of the sample distribution connection channels. Through holes are additionally opened on the upper-layer chip and vertically run through it at positions corresponding to inlets of the reaction chamber sample input channels, to form sample outlet holes of the sample distribution connection channels. In addition, the upper-layer chip is further provided with an overflow passage sample inlet hole running through the reaction pool upper cover, and an overflow passage sample outlet hole that vertically running through runs through the upper-layer chip. In other words, the overflow passage sample inlet hole, overflow passage sample outlet hole, sample inlet hole of the sample distribution connection channel, and sample outlet hole of the sample distribution connection channel are all through holes that vertically run through the upper-layer chip. Moreover, the overflow passage sample inlet hole is communicated with the reaction pool, the sample inlet hole of the sample distribution connection channel is communicated with the outlet of the sample distribution chamber sample output channel, and the sample outlet hole of the sample distribution connection channel is communicated with the inlet of the reaction chamber sample input channel.

Figure 9:
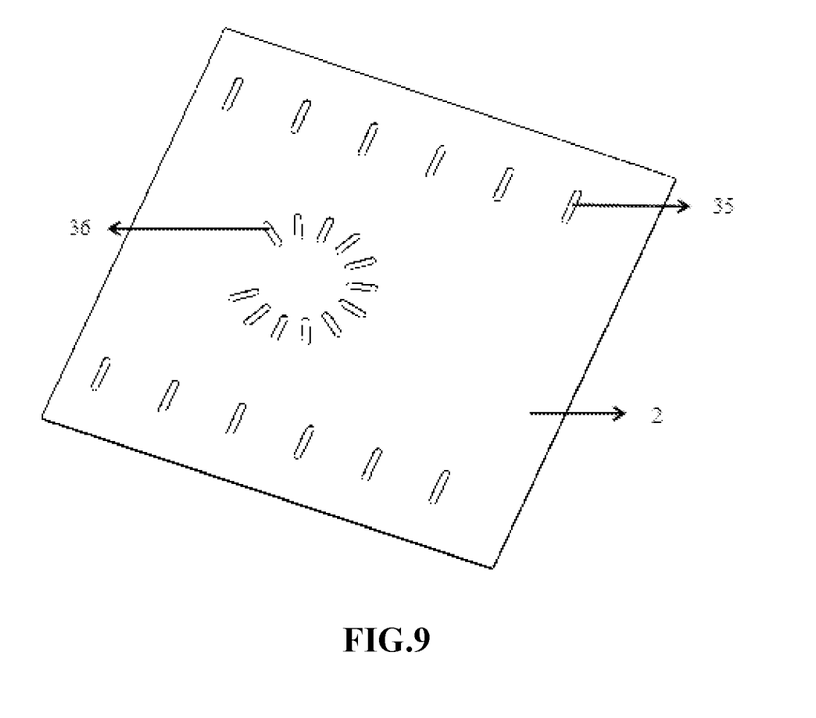
FIG. 9 is a schematic structural diagram of an upper thin film.

The upper thin film covers an upper surface of the reaction zone of the upper-layer chip, and a sample distribution connection passage can be formed between the sample inlet hole of the sample distribution connection channel and the sample outlet hole of the sample distribution connection channel after the upper thin film undergoes heat sealing processing by a heat sealing device. At the same time, an overflow passage is formed between the corresponding overflow passage sample inlet hole and overflow passage sample outlet hole. A detailed specific structure is as shown in FIG. 9. It can be known that, the overflow passage and the sample distribution connection passage each include two parts: a thin film part and an upper-layer chip part corresponding to the thin film part. In addition, the thin film part of the sample distribution connection passage can form a sample distribution occlusion portion after undergoing heat sealing processing by the heat sealing device, to intercept the flow in the sample distribution channels. The thin film part of the overflow passage can form an overflow occlusion portion after undergoing heat sealing processing by the heat sealing device, to intercept the flow at the outlet of the reaction chamber.

Figure 2:
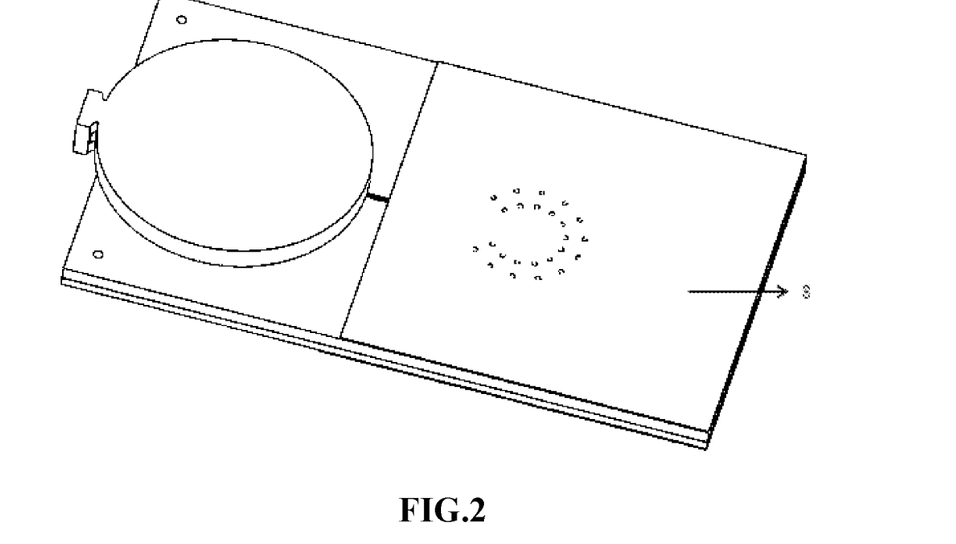
FIG. 2 is a schematic integral diagram of the microfluidic chip for nucleic acid detection according to the present invention.
Figure 3:
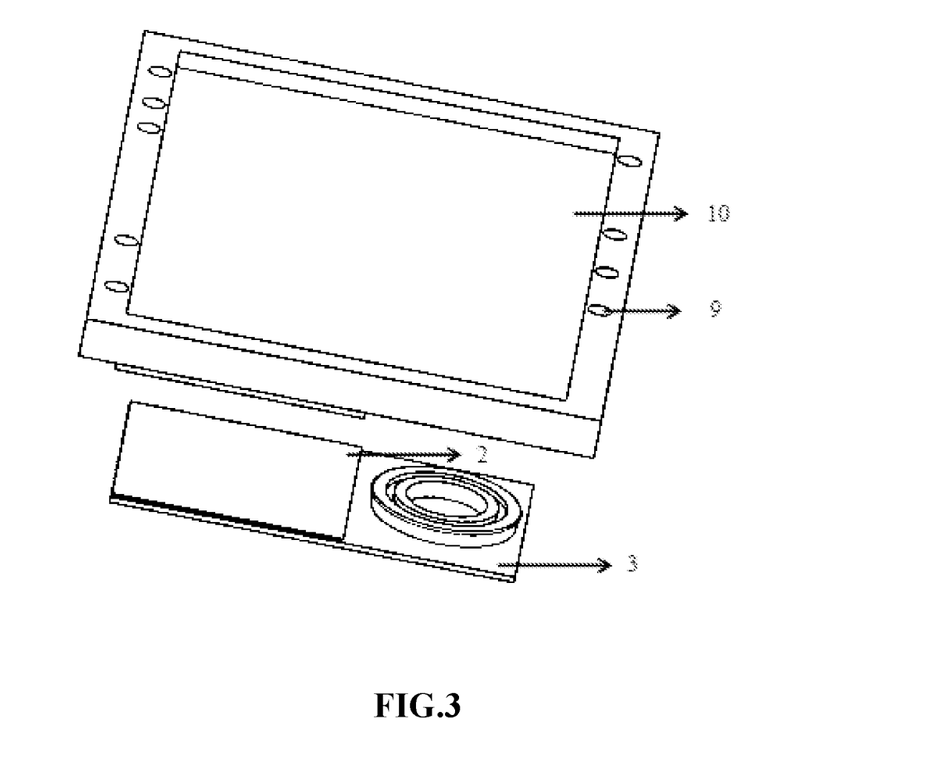
FIG. 3 is a schematic structural diagram showing that a heat sealing device is used to perform heat sealing processing for the chip body, where In the figure: Upper thin film 2; Upper-layer chip 3; Heat-sealing cover connector 9; Heat-sealing cover 10.
Figure 4:
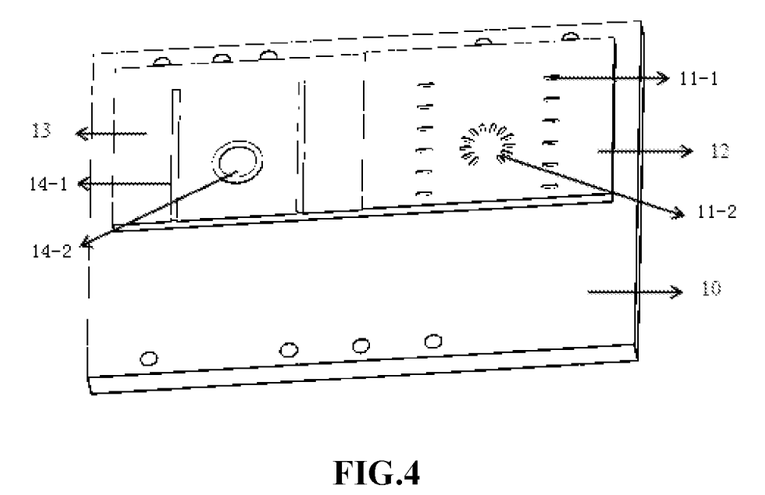
FIG. 4 is a schematic structural diagram of a heat sealing device.

As shown in FIGS. 2, 3, and 4, the heat sealing device includes a heat sealing cover provided with a channel block and a heat sealing block.

The channel block is provided with mold recesses a and mold recesses b. The mold recess a matches up with the sample distribution connection passage in size, and a distribution condition of the mold recesses a on the channel block is consistent with that of the sample distribution connection passages on the upper-layer chip. The mold recess b matches up with the overflow passage in size, and a distribution condition of the mold recesses b on the channel block is consistent with that of the overflow passages on the upper-layer chip.

The heat sealing block is provided with a mold protrusion a and a mold protrusion b. The mold protrusion a includes two protruding bars, and the two protruding bars can respectively press against thin film parts of the overflow passages in two rows. The mold protrusion b is an annular protrusion that can press against thin film parts of the sample distribution connection passages.

An upper surface of the lower-layer chip is provided with a through hole in communication with the filter element passage on a position corresponding to each overflow passage sample outlet hole.

The number of the filter element passages is the same as that of the overflow passage sample outlet holes, and the filter element passages are arranged below the overflow passage sample outlet holes in rows. The filter element passages are arranged on the lower surface of the lower-layer chip, a breathable and liquid-impermeable filter element is provided in each filter element passage, and liquid outlets of the filter element passages in each row converge in communication with a test paper passage.

The test paper passage is provided on the back side of the lower-layer chip, and positioned outside of the filter element passage.

A specific embodiment involved in the present invention is described in detail below with reference to FIG. 1 to FIG. 9.

The multi-flux microfluidic chip for nucleic acid detection described in this embodiment includes an upper-layer and lower-layer chip, and an upper and lower thin film, which are successively an upper thin film 2, an upper-layer chip 3, a lower-layer chip 4, and a lower thin film 7 from top to bottom. The upper-layer chip and the lower-layer chip are integrated after insertion through alignment holes, and are bonded by a technique such as heat bonding, ultrasound or laser. After the upper thin film 2 and the upper-layer chip 3 are heated by a heat sealing cover 10 to reach a high temperature, overflow channels 35 and sample distribution connection channels 36 are formed through heat sealing for the channel block 12. A sample input chamber, a rationing chamber (which is further a chamber for storing a reaction reagent, and therefore also called "reaction and rationing chamber"), and a liquid channel are formed between the upper-layer chip 3 and the lower-layer chip 4. The lower-layer chip 4 and the lower thin film 7 are bonded by a technique such as heat bonding, ultrasound or laser, to form a lower surface of a reaction chamber, a liquid channel, test paper passages, and filter element passages. The sample input chamber is used for storing a sample. An air path connector 19 is disposed on the sample input chamber, and the sample input chamber is connected to an air path through the air path connector 19 after completion of sample loading. Then, the sample is delivered to a through hole 18 and finally enters the channel under thrust of an air pump.

The chip is provided with 12 reaction chambers, the reaction chamber being formed by bonding a reaction pool upper cover 22 disposed on the upper-layer chip, a reaction pool 25 disposed on the lower-layer chip, and a reaction pool bottom disposed on the lower thin film. The lower thin film is made from a thin-layer polymer material such as PP, PE, or PS. A reaction dry powder reagent required for a reaction is pre-embedded in each reaction chamber, where the dry powder reagent includes an enzyme, primer, probe and various buffer solutions required for a PCR reaction. During reaction in the reaction chamber, a reaction liquid expands with heat, and the lower thin film deforms to a certain degree for mitigation. After completion of the reaction, data is read through fluorescence detection.

The sample distribution connection channel 36 is formed through heat sealing by the heat sealing cover 10 for the upper thin film and the upper-layer chip. The sample distribution connection channel 36 has no depth, and is formed by the upper-layer chip directly contacting the upper thin film with no gap. The sample distribution connection channel 36 provides resistance to a certain degree, so that the sample is distributed from one place to multiple channels. The sample is added to the sample input pool 17, enters the sample output main channel 27 through the sample output through hole 18, and flows from the sample distribution chamber sample output channels 29 through the sample distribution connection channels 36 to the upper-layer chip, to distribute the flow. Afterwards, the sample enters reaction pool sample input channels 28 on the lower-layer chip through sample outlet holes 15 of the sample distribution connection channels on the upper-layer chip. Finally, the sample flows to the reaction pools 25. Then, when the reaction pool is filled with the sample, the sample can enter overflow passages 35 disposed on the upper-layer chip through overflow passage sample inlet holes, so as to discharge air out of the reaction chambers and make a ration. After completion of rationing in the reaction chambers, the reaction chambers are closed under the effect of the heat sealing cover.

A breathable and liquid-impermeable filter element is inserted in the filter element passage 34, where the filter element is made from PP, glass fiber, PE, or a high-molecular polymer material. After the sample enters lower ends 30 of connection through holes of the filter element passages and finally reaches the filter element passages 34, the sample is intercepted at the filter element, so that the sample is equally distributed among the 12 reaction chambers.

Water-absorption color indicator paper is placed in the test paper passage 33 in advance, which may be used as a quality inspection measure for the microfluidic chip. In a normal case, the sample flows down to the filter element passages 34 and is stopped by the filter element, and there is no seepage of the sample. When the chip has a fault, the sample seeps out of the filter element, and the color indicator paper placed in the test paper passage 33 shows a color, to indicate an invalid reaction of the chip this time, thus preventing errors and aerosol pollution.

The heat sealing block 13 is provided on the heat sealing cover. After rationing completion of the added sample, the plug 1 is closed, and the heat sealing block 13 is heated. The microfluidic chip is placed on a fixed support. Pressed by the heat sealing block, the mold protrusions a 14-1 and b 14-2 separately contact the upper thin film, thin film channels on the chip are heat-sealed by the mold protrusions a 14-1 and b 14-2, and channels at two ends of the reaction chamber are closed. Thus, no cross contamination is caused to the reagent when it is subjected to PCR reaction in the reaction chambers. After completion of the reaction, fluorescence detection is performed above the 12 reaction chambers to obtain a result.

Another technical objective of the present invention is to provide a method of using a multi-flux microfluidic chip for nucleic acid detection and capable of actively controlling a flow path, which includes the following steps:

1) An upper-layer chip and a lower-layer chip are assembled into a whole in a bonding manner.

2) A channel block of a heat sealing device is used to perform heat sealing processing on an upper thin film, such that overflow passages and sample distribution connection passages are formed between the upper thin film and the upper-layer chip. In this case, a microfluidic channel between a sample loading pool and a reaction pool is in an opened state, and a microfluidic channel between the reaction pool and a filter element passage is also in an opened state.

3) A reaction dry powder reagent required for a PCR reaction is pre-embedded in the reaction pool of the lower-layer chip, a breathable and liquid-impermeable filter element is pre-disposed in the filter element passage, and color indicator paper is pre-disposed in a test paper passage.

4) A reaction zone of a lower surface of the lower-layer chip is covered with a lower thin film, and heat sealing processing is performed.

5) A sample is added into the sample loading pool.

6) An external air path is mounted at a sample inlet of the sample loading pool. The external air path is then connected to an air source, and under an air pressure provided by the air source, the sample in the sample loading pool passes through a sample output main channel and a sample distribution chamber successively, and flows to a corresponding reaction pool through sample distribution chamber sample output channels, the sample distribution connection passages, and reaction chamber sample input channels. After the sample flowing out of the reaction pools enters the filter element passages through the overflow passages, an instrument stops the flow of the external air path by detecting a pressure value.

7) A heat sealing block of the heat sealing device is used to perform heat sealing processing on the upper thin film, such that an overflow occlusion portion is formed between a thin film part of each overflow passage and the upper-layer chip, and a sample distribution occlusion portion is formed between a thin film part of each sample distribution connection passage and the upper-layer chip. In this case, the front end and the rear end of the reaction pool are both in a flow intercepted state and the reaction pools are closed.

8) A chip plug is closed.

9) The sample and the reaction dry powder reagent in the reaction pool produce a PCR reaction.

10) Fluorescent data is read after completion of the reaction.

What is claimed is:

1. A multi-flux microfluidic chip for nucleic acid detection and capable of actively controlling a flow path, the multi-flux microfluidic chip comprises: a chip body, comprises a sample loading chamber, a plurality of reaction chambers, and a microfluidic channel, wherein the sample loading chamber is communicated with an external air path and a sample output through hole of the sample loading chamber is communicated with the reaction chambers through the microfluidic channel; wherein the microfluidic channel comprises a sample output main channel and several sample distribution channels disposed in one-to-one correspondence to the reaction chambers; the sample distribution channels are separately disposed, and comprise sample distribution chamber sample output channels and reaction chamber sample input channels; wherein:

one end of the sample output main channel is communicated with the sample output through hole of the sample loading chamber, and another end is communicated with a sample distribution chamber;

the reaction chambers are arranged in two rows that are symmetrically distributed on two sides of the sample distribution chamber with the axis of the sample output main channel as a line of symmetry;

the sample distribution chamber sample output channels of the sample distribution channels are evenly distributed on the periphery of the sample distribution chamber, and the reaction chamber sample input channels are symmetrically arranged on two sides of the sample distribution chamber with the axis of the sample output main channel as a line of symmetry; and     a sample distribution connection channel disposed on the chip body, each of the sample distribution chamber sample output channels and its corresponding reaction chamber sample input channel are communicated through the sample distribution connection channel; each of the sample distribution connection channel extends across the corresponding sample distribution chamber sample output channel and reaction chamber sample input channel; and a thin film part of the sample distribution connection channel forms a sample distribution occlusion portion to intercept the flow in the sample distribution channels;

the chip body comprises an upper thin film, an upper-layer chip, a lower-layer chip, and a lower thin film; wherein:

the upper-layer chip is partitioned into a sample loading zone and a reaction zone; a sample loading pool is disposed on the sample loading zone of the upper-layer chip, a plug is configured in a sample loading hole of the sample loading pool, when the plug is configured in the sample loading hole of the sample loading pool, the plug and the sample loading pool constitute the sample loading chamber, and the sample output through hole of the sample loading chamber is disposed on the bottom of the sample loading pool; the reaction zone of the upper-layer chip comprises a sample inlet hole of the sample distribution connection channel and a sample outlet hole of the sample distribution connection channel separately; the sample output through hole of the sample loading chamber, the sample inlet hole of the sample distribution connection channel, and the sample outlet hole of the sample distribution connection channel are all through holes vertically running through the upper-layer chip;

the lower-layer chip is located below the upper-layer chip, and is connected to a lower surface of the upper-layer chip in a bonding manner; and the lower-layer chip is provided with a lower-layer chip reaction zone on a position corresponding to the reaction zone of the upper-layer chip;

the lower-layer chip reaction zone comprises a sample distribution pool, a plurality of reaction pools, the sample distribution chamber sample output channel, and the reaction chamber sample input channel; the lower surface of the upper-layer chip covers the sample distribution pool to form a sample distribution chamber, and the sample distribution pool is communicated with the sample output through hole disposed on the bottom of the sample loading pool through the sample output main channel disposed on the lower-layer chip;

the upper-layer chip includes a plurality of reaction pool upper covers;

the reaction pool upper covers correspond to the reaction pools, and the lower thin film is in close contact with the reaction pools to folin the reaction chambers;

the sample inlet hole of the sample distribution connection channel is disposed directly above the sample outlet of the sample distribution chamber sample output channel, and the sample outlet hole of the sample distribution connection channel is disposed directly above the sample inlet of the reaction chamber sample input channel; and the upper thin film covers an upper surface of the reaction zone of the upper-layer chip, and a sample distribution connection passage is formed between the sample inlet hole of the sample distribution connection channel and the sample outlet hole of the sample distribution connection channel; in addition, a thin film part of the sample distribution connection passage forms a sample distribution occlusion portion to intercept the flow in the sample distribution passage.

2. The multi-flux microfluidic chip for nucleic acid detection and capable of actively controlling a flow path according to claim 1, wherein the chip body further comprises a filter element passage and a test paper passage in communication with a liquid outlet of the filter element passage; wherein a breathable and liquid-impermeable filter element is provided in the filter element passage, and color indicator paper is provided in the test paper passage; the reaction chamber comprises an outlet, and the outlet of the reaction chamber communicates with an inlet of the filter element passage through an overflow passage, a part of the upper thin film serves as the overflow passage, the overflow passage extending across the outlet of the reaction chamber and the inlet of the filter element passage; and a thin film part of the overflow passage forms an overflow occlusion portion after undergoing heat sealing processing, to intercept the flow at the outlet of the reaction chamber.

3. The multi-flux microfluidic chip for nucleic acid detection and capable of actively controlling a flow path according to claim 2, wherein each of the filter element passage is disposed corresponding to each of the reaction chambers, and the liquid outlets of the filter element passages converge in communication with the test paper passage; and there are two test paper passages that are correspondingly arranged outside of the two rows of the reaction chambers.

4. The multi-flux microfluidic chip for nucleic acid detection and capable of actively controlling a flow path according to claim 1, wherein the lower thin film covers a lower surface of a reaction zone of the lower-layer chip, and the lower thin film serves as the bottom of each of the reaction pools.

5. The multi-flux microfluidic chip for nucleic acid detection and capable of actively controlling a flow path according to claim 1, wherein for each of the reaction pools, the reaction zone of the upper-layer chip is provided with an overflow passage sample inlet hole and an overflow passage sample outlet hole; and the overflow passage sample inlet hole and the overflow passage sample outlet hole are both through holes vertically running through the upper-layer chip, and the overflow passage sample inlet hole is arranged to just run through the reaction pool upper cover;

overflow passage can be formed between the corresponding overflow passage sample inlet hole and overflow passage sample outlet hole; and in addition, a thin film part of the overflow passage can also form an overflow occlusion portion to intercept the flow at the outlet of the reaction chamber;

the overflow passages are arranged in two rows that are correspondingly distributed outside of the corresponding reaction pool;

an upper surface of the lower-layer chip is provided with a through hole in communication with the filter element passage on a position corresponding to each overflow passage sample outlet hole;

the number of the filter element passages is the same as that of the overflow passage sample outlet holes, and the filter element passages are arranged below the overflow passage sample outlet holes in rows; the filter element passages are arranged on the lower surface of the lower-layer chip, a breathable and liquid-impermeable filter element is provided in each filter element passage, and liquid outlets of the filter element passages in each row converge in communication with a test paper passage; and the test paper passage is provided on the back side of the lower-layer chip, and positioned outside of the filter element passage.

6. The multi-flux microfluidic chip for nucleic acid detection and capable of actively controlling a flow path according to claim 5, wherein the heat sealing device comprises a heat sealing cover provided with a channel block and a heat sealing block, wherein:

the channel block is provided with first mold recesses and second mold recesses; the first mold recess matches up with the sample distribution connection passage in size, and a distribution condition of the first mold recesses on the channel block is consistent with that of the sample distribution connection passages on the upper-layer chip; the second mold recess matches up with the overflow passage in size, and a distribution condition of the second mold recesses on the channel block is consistent with that of the overflow passages on the upper-layer chip; and the heat sealing block is provided with a first mold protrusion and a second mold protrusion; the first mold protrusion comprises two protruding bars, and the two protruding bars are respectively pressed against thin film parts of the overflow passages in two rows; the second mold protrusion is an annular protrusion that pressed against thin film parts of the sample distribution connection passages.

7. The multi-flux microfluidic chip for nucleic acid detection and capable of actively controlling a flow path according to claim 1, wherein the upper-layer chip and the lower-layer chip are integrally bonded by connecting a cylinder and a positioning hole in a fitted manner.

8. The multi-flux microfluidic chip for nucleic acid detection and capable of actively controlling a flow path according to claim 1, wherein a reaction dry powder reagent required for a polymerase chain reaction (PCR) is pre-embedded in the reaction chamber, the reagent comprising an enzyme, primer, probe and buffer solution required for the PCR reaction.

* * * * *